(12) United States Patent
Elghazzawi et al.

(10) Patent No.: US 9,843,026 B2
(45) Date of Patent: Dec. 12, 2017

(54) BATTERY MODULE

(75) Inventors: Ziad F. Elghazzawi, Newton, MA (US); Jing Pan, Newton, MA (US); Peter A. Lund, Nashua, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 378 days.

(21) Appl. No.: 13/555,436

(22) Filed: Jul. 23, 2012

(65) Prior Publication Data
US 2013/0053909 A1 Feb. 28, 2013

Related U.S. Application Data

(60) Provisional application No. 61/527,655, filed on Aug. 26, 2011.

(51) Int. Cl.
*A61N 1/39* (2006.01)
*A61N 1/378* (2006.01)
*H01M 2/10* (2006.01)

(52) U.S. Cl.
CPC ........ *H01M 2/1061* (2013.01); *A61N 1/3975* (2013.01); *A61N 1/3981* (2013.01)

(58) Field of Classification Search
CPC . H01M 2/1061; A61N 1/36125; A61N 1/375; A61N 1/39; A61N 1/3975; A61N 1/3981
USPC ...................................... 607/5; 320/103, 125
See application file for complete search history.

(56) References Cited

U.S. PATENT DOCUMENTS 5,314,451 A * 5/1994 Mulier .................... A61N 1/378 607/33
5,853,915 A * 12/1998 Suto ................................ 429/99
6,044,923 A * 4/2000 Reagan et al. ........... 180/65.265
6,201,992 B1 * 3/2001 Freeman ............................ 607/5
6,271,644 B1 * 8/2001 Okada ................... H01M 2/105 320/112
6,441,582 B1 * 8/2002 Powers ................ A61N 1/3975 320/112
6,472,880 B1 * 10/2002 Kang ................. G01R 31/3658 324/434

(Continued)

OTHER PUBLICATIONS

International Search Report & Written Opinion, PCT/US2012/047812, dated Oct. 5, 2012, 15 pages.

*Primary Examiner* — William Levicky
(74) *Attorney, Agent, or Firm* — Zoll Medical Corporation

(57) ABSTRACT

An external defibrillator comprising: a unit for providing electrical stimulation of a patient; a battery module that includes: a battery housing; a plurality of battery banks within the housing, each of the battery banks being electrically isolated from each of the other battery banks within the housing and having a total lithium content of less than an amount requiring special handling procedures during transportation and storage; and a plurality of pairs of electrical contacts external to the housing, each of the pairs of electrical contacts being configured to provide an electrical connection to an associated battery bank; and a connector unit external to the battery housing that includes: a plurality of pairs of electrical contacts configured to mate with the plurality of pairs of electrical contacts of the battery module; and circuitry electrically connecting the plurality of pairs of electrical contacts of the connector unit to provide a single voltage output to the unit for providing electrical stimulation.

13 Claims, 7 Drawing Sheets

(56) References Cited

U.S. PATENT DOCUMENTS

| | | | |
|---|---|---|---|
| 6,873,133 B1 | 3/2005 | Kavounas | |
| 6,884,540 B2* | 4/2005 | Chikada | 429/99 |
| 6,891,350 B2* | 5/2005 | George | H02J 7/0034 |
| | | | 320/105 |
| 7,095,210 B2* | 8/2006 | Tamura | A61N 1/3975 |
| | | | 320/103 |
| 8,032,230 B1* | 10/2011 | Cox et al. | 607/116 |
| 2003/0162086 A1* | 8/2003 | Longhi et al. | 429/94 |
| 2007/0141452 A1* | 6/2007 | Kim | H01M 2/0202 |
| | | | 429/120 |
| 2010/0198286 A1* | 8/2010 | Neumiller | A61N 1/3931 |
| | | | 607/5 |
| 2010/0198287 A1* | 8/2010 | Neumiller et al. | 607/5 |

\* cited by examiner

BATTERY MODULE

CROSS-REFERENCE TO RELATED APPLICATIONS

This is a utility of U.S. Provisional Application Ser. No. 61/527,655 filed Aug. 26, 2011. All subject matter set forth in the above referenced application is hereby incorporated by reference into the present application as if fully set forth herein.

TECHNICAL FIELD

This document relates to batteries, e.g., batteries for medical devices such as defibrillators. More particularly, this document relates to systems, circuitry, battery modules, and/or techniques for providing batteries capable of providing sufficient voltage and current without being classified as hazardous material for shipping.

BACKGROUND

Batteries are used in various types of devices ranging from small scale electronic devices to laptops to medical devices and even to electric powered vehicles. The types and size of the batteries used in these various applications depends on the voltage and current required by the battery operated device.

A battery includes an anode, a cathode, an electrolyte and a housing. Batteries can be rechargeable or non-rechargeable depending on the design of the battery and the materials used in the battery. A non-rechargeable battery, also referred to as a primary battery, is discarded at the end of its operational life. A rechargeable battery, also referred to as a secondary battery, is recharged after discharge throughout its operational use. Once a battery chemistry is chosen, a number of individual batteries may be connected in series, parallel, or series and parallel to form a battery module.

One exemplary type of battery is a lithium battery. Lithium batteries are batteries that have lithium metal or lithium compounds as an anode. Depending on the design and chemical compounds used, lithium banks often produce voltages from 1.5 V to about 3.7 V. Lithium batteries are commonly used in products such as portable consumer electronic devices. Lithium batteries can provide extremely high currents and can discharge very rapidly when short-circuited. Although this is useful in applications where high currents are required, a too-rapid discharge of a lithium battery can result in overheating of the battery, rupture, and even explosion.

The United States Department of Transportation (DOT) regulates the transportation of materials in the United States. Currently, for Lithium batteries the USDOT requires at most 8 g lithium in the battery package in order to ship the battery without additional requirements. If over 8 g of Lithium are in the battery package, the battery is classified as a Class 9 shipment and requires special labeling, packaging, markings, and paperwork. Additionally, for a class 9 shipment, the shipper must list an emergency number and be sure it is monitored while the hazardous material is in transport. Further, hazmat training is required for employees working with Class 9 materials. Thus, shipment of lithium batteries exceeding the 8 g lithium limit can be complicated by the shipping restrictions imposed by the DOT. UN transportation regulatory requires that batteries with lithium contents of more than 2 g be handled and shipped as class 9 internationally.

SUMMARY

This document describes systems and techniques that may be used to provide Lithium battery modules with lithium amounts below the amounts requiring special transportation/handling regulations such as class 9 shipping requirements.

In some aspects, an external defibrillator includes a unit for providing electrical stimulation of a patient. The external defibrillator also includes a battery module that includes a battery housing, a plurality of battery banks within the housing, each of the battery banks being electrically isolated from each of the other battery banks within the housing and having a total lithium content of less than an amount requiring special handling procedures during transportation and storage, and a plurality of pairs of electrical contacts external to the housing, each of the pairs of electrical contacts being configured to provide an electrical connection to an associated battery bank. The external defibrillator also includes a connector unit external to the battery housing that includes a plurality of pairs of electrical contacts configured to mate with the plurality of pairs of electrical contacts of the battery module and circuitry electrically connecting the plurality of pairs of electrical contacts of the connector unit to provide a single voltage output to the unit for providing electrical stimulation.

Embodiments can include one or more of the following.

The connector unit can be included within a housing of the unit for providing electrical stimulation.

The connector unit can be separate from both a housing of the unit for providing electrical stimulation and the battery module.

The housing can include a plurality of physically separated compartments, each of the compartments being configured to house one of the plurality of battery banks.

Each of the battery banks can include two or more lithium cells connected in series.

Each of the battery banks can include two or more lithium cells connected in parallel.

The module can include six battery banks with each of the six battery banks including two lithium cells connected in series and the electrical connectors are configured to connect pairs of the battery banks in series and to connect the series pairs of battery banks in parallel.

The module can include four battery banks with each of the four battery banks including three lithium cells connected in parallel and the electrical connectors are configured to the six battery banks in series.

The total lithium content of any one of the battery banks can be less than 2 g.

The total lithium content of any one of the battery banks can be less than 8 g.

The total lithium content of any one of the battery banks can be less than 3 g.

The total lithium content of any one of the battery banks can be less than an amount requiring special handling procedures during transportation.

The circuitry electrically connecting the plurality of pairs of electrical contacts of the connector unit can include jumper wires.

In some additional aspects, a battery module includes a housing and a plurality of battery banks within the housing, each of the battery banks being electrically isolated from each of the other battery banks within the housing and each of the battery banks including two or more electrically connected lithium cells with a total lithium content of the two or more lithium cells in any one of the battery banks being less than 8 g or less than an amount requiring special handling procedures during transportation and storage. The battery module also includes a plurality of pairs of electrical contacts external to the housing, each of the pairs of electrical contacts being configured to provide an electrical connection to an associated battery bank of the plurality of battery banks.

Embodiments can include one or more of the following.

The battery banks can be configured to be electrically connected by a set of electrical connectors external to the housing.

The housing can include a plurality of physically separated compartments, each of the compartments being configured to house one of the plurality of battery banks.

The two or more lithium cells in a particular battery bank of the plurality of battery banks can be connected in series.

The two or more lithium cells in a particular battery bank of the plurality of battery banks can be connected in parallel.

The module can include exactly eight battery banks with each of the eight battery banks including exactly two lithium cells connected in series.

The module can include exactly six battery banks with each of the six battery banks including exactly three lithium cells connected in parallel.

The total lithium content of the two or more lithium cells in any one of the battery banks can be less than 5 g.

The total lithium content of the two or more lithium cells in any one of the battery banks can be less than 2 g.

The total lithium content of the two or more lithium cells in any one of the battery banks is less than an amount requiring special handling procedures during transportation and storage.

DETAILED DESCRIPTION

This document describes battery modules, e.g., battery modules for medical devices such as defibrillators, designed to have lithium contents below a particular threshold associated with shipping or other hazardous material limitations. More particularly, this document relates to systems, circuitry, battery modules, and/or techniques for providing batteries capable of providing sufficient voltage and current without being classified as hazardous material for shipping (e.g., without being classified as a class 9 shipment).

Various countries have restrictions on the transport of Li-ion batteries based on the amount of lithium included in the battery or battery module. For example, currently in the U.S., transporting any battery including more than 8 g of Lithium requires specialized treatment and training. UN transportation regulatory requires that batteries with lithium contents of more than 2 g be handled and shipped as class 9. In general, single Li-ion batteries are often constructed such that the battery does not exceed the limits. However, in many applications, a voltage and/or current in excess of that provided by a single battery can be desired to power a device (e.g., to power a defibrillator). In order to provide a voltage that is greater than the voltage of a single battery, multiple batteries are often connected in series to produce a voltage output about equal to a sum of the outputs from each of the individual batteries. Further, in order to increase the current output from a battery module, multiple batteries are often connected in parallel. Thus, after connecting multiple batteries to form the battery module with the desired voltage/current, often the constructed module is in excess of the Lithium limits.

Figure 1:
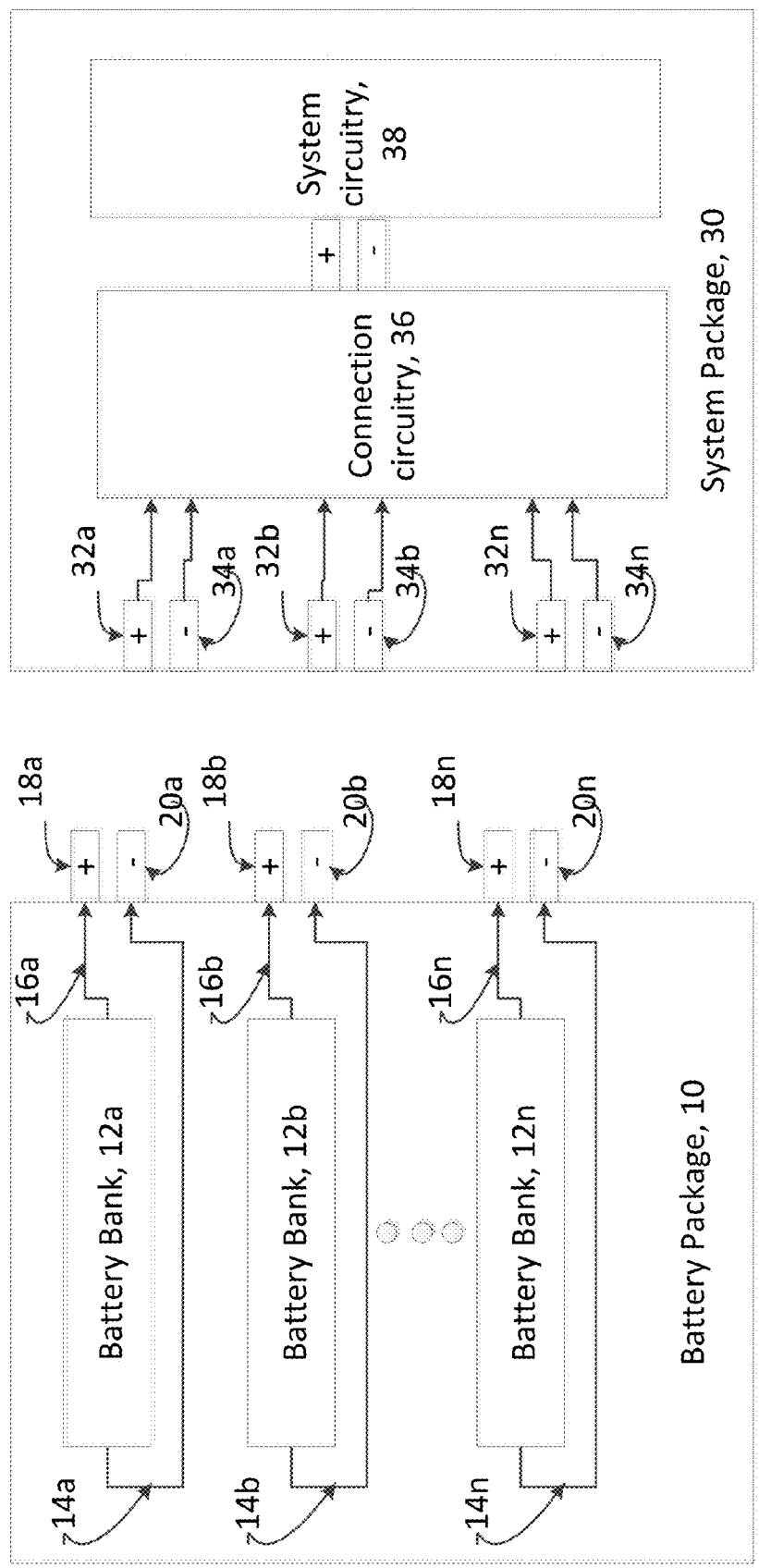
FIG. 1 shows an exemplary battery package and system package.

FIG. 1 shows an exemplary battery module configured to have lithium contents below the lithium shipping thresholds while providing adequate voltage and currents. A battery package 10 includes multiple battery banks 12a-12n each of which includes one or more Li-ion batteries electrically connected either in series or parallel. The number of Li-ion batteries in each of the battery banks 12a-12n is selected based on a lithium content of each of the batteries such that the total lithium content for the bank is below the acceptable lithium threshold. For example, the maximum number of batteries electrically connected within a bank can be determined such that: Lithium threshold>number of batteries in a bank*grams lithium in single battery. For example, in order to avoid classification as a class 9 device, the total lithium content must be less than 2 g (e.g., the Lithium threshold would be 2 g). If each Li-ion battery in a bank included 0.6 g of lithium, no more than 3 batteries would be electrically connected within a bank (e.g., 3*0.6 g<2 g).

Electrical connections between the multiple battery banks are not formed within the battery package 10. Rather, the battery banks 12a-12n are electrically isolated from one another. Each of the banks is connected to electrically and physically separate external connectors 18a-18n and 20a-20n. In some embodiments, in addition to having an electrical separation between the battery banks 12a-12n, the battery banks can also be physically separated for example by a plastic baffle or wall within the package 10. Thus, even though a sum of the lithium content for each of the batteries in the battery package 10 may exceed the lithium threshold (e.g., a number of batteries per bank*grams lithium in single battery*number of banks may exceed the threshold), because the multiple banks are not electrically connected within the battery package 10 and each of the battery banks has a total lithium amount less than the lithium threshold amount, the battery module is not classified as a hazardous device (e.g., is not classified as a class 9 device for shipping).

Due to the lack of internal connections between the battery banks, the battery package includes multiple external connections with each connection being associated with a particular battery bank. However, a single pair one of the of positive/negative connections from the battery package 10 is unlikely to provide the voltage and current required by the device to be powered. As such, at a location outside of the battery package the desired connections between the battery banks can be formed. These connections can be formed subsequent to shipping of the battery package 10 such that the battery banks are physically and electrically isolated from each other during shipping.

FIG. 1 shows an example of a system package 30 that includes multiple pairs of connectors (e.g., 32a/34a; 32b/34b . . . 32n/34n) configured to mate with the connectors of the battery package 10. For example, the connectors on the battery package 10 can be male connectors and the connectors on the system package can be female connectors. The connectors in the system package form an electrical connection between the battery banks 12a-12n in the battery package 10 and connection circuitry 36 in the system package. The connection circuitry 36 forms electrical connections between the banks 12a-12n in the battery package 10 and provides an output having a voltage and current for driving system circuitry 38. As such, the connection circuitry 36 forms the electrical connections between the battery banks inside the system package 30 (e.g., as opposed to the electrical connections between the battery banks being formed in the battery package 10).

For example, a battery package can include N batteries where the lithium content of all of the N batteries exceeds a lithium threshold (e.g., is greater than 2 g) but the lithium content (m) in a single battery does not exceed the lithium threshold (e.g., is less than 2 g). Based on this example, the total lithium content in the battery package is N*m; and N*m>2 g. However, the lithium content in single battery is m<2 g. Multiple individual batteries can be grouped together to form an electrically connected subgroup referred to herein as a battery bank with 'a' representing the number of batteries in the battery bank. Assuming that the constraint of a*m<the threshold lithium content (e.g., a*m<2 g), multiple individual batteries can be grouped together to form a battery bank with the battery bank still having a lithium content less than the acceptable threshold. No electrical connections exist between the battery banks within the battery housing and the battery banks are mechanically isolated. Each of the battery banks has two connections out to the battery package (e.g., positive and negative terminals). When the battery package plugs into the system the desired connections between the battery banks can be formed inside the system.

Figure 2:
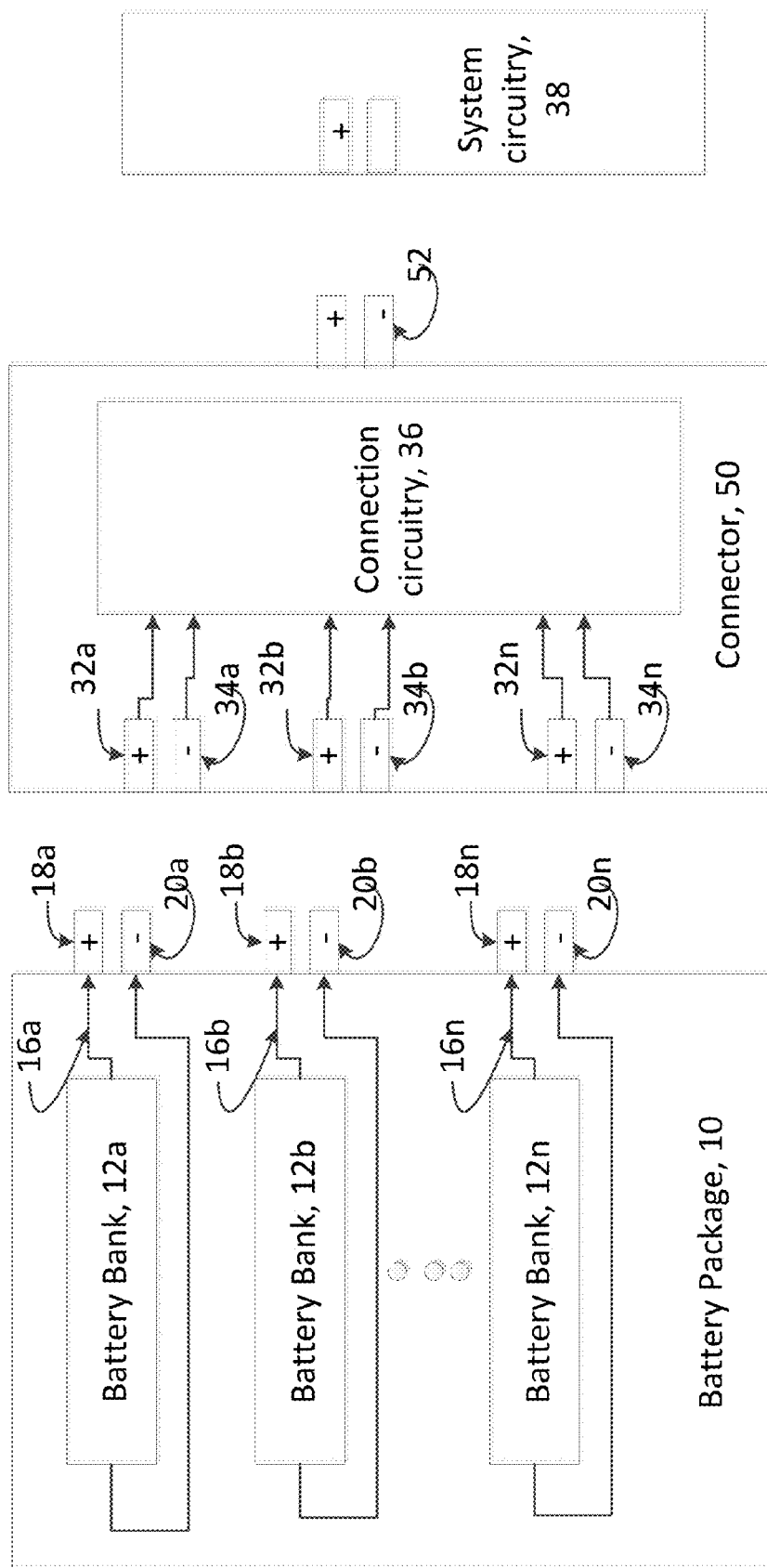
FIG. 2 shows an exemplary battery package, connector, and system.

While in the arrangement shown in FIG. 1 the connections between the multiple battery banks in the battery package 10 were formed internal to the system package 30 other arrangements are possible. For example, as shown in FIG. 2, a separate connector 50 can include the connectors (e.g., connectors 32a-32n and 34a-34n) to mate with the respective connectors of the battery package (e.g., connectors 18a-18n and 20a-20n). The connector 50 can also include connection circuitry 36 (e.g., as described in relation to FIG. 1) to form the connections between the battery banks at a location outside of the battery package 10. Thus, the connector 50 receives multiple voltage inputs and forms connections between the inputs to provide a single voltage output 52. The single output 52 can be connected to system circuitry in the same manner that a battery package with internal connections between each of the batteries would be connected to the system circuitry 38. As such, in the arrangement shown in FIG. 2, no changes or modifications are needed to the system to be powered (e.g., to the system circuitry). Rather, an intermediate connection device (e.g., connector 50) forms the electrical connections that are missing (e.g., intentionally omitted from inside the battery package due to lithium restrictions) from the battery package 10.

Figure 3:
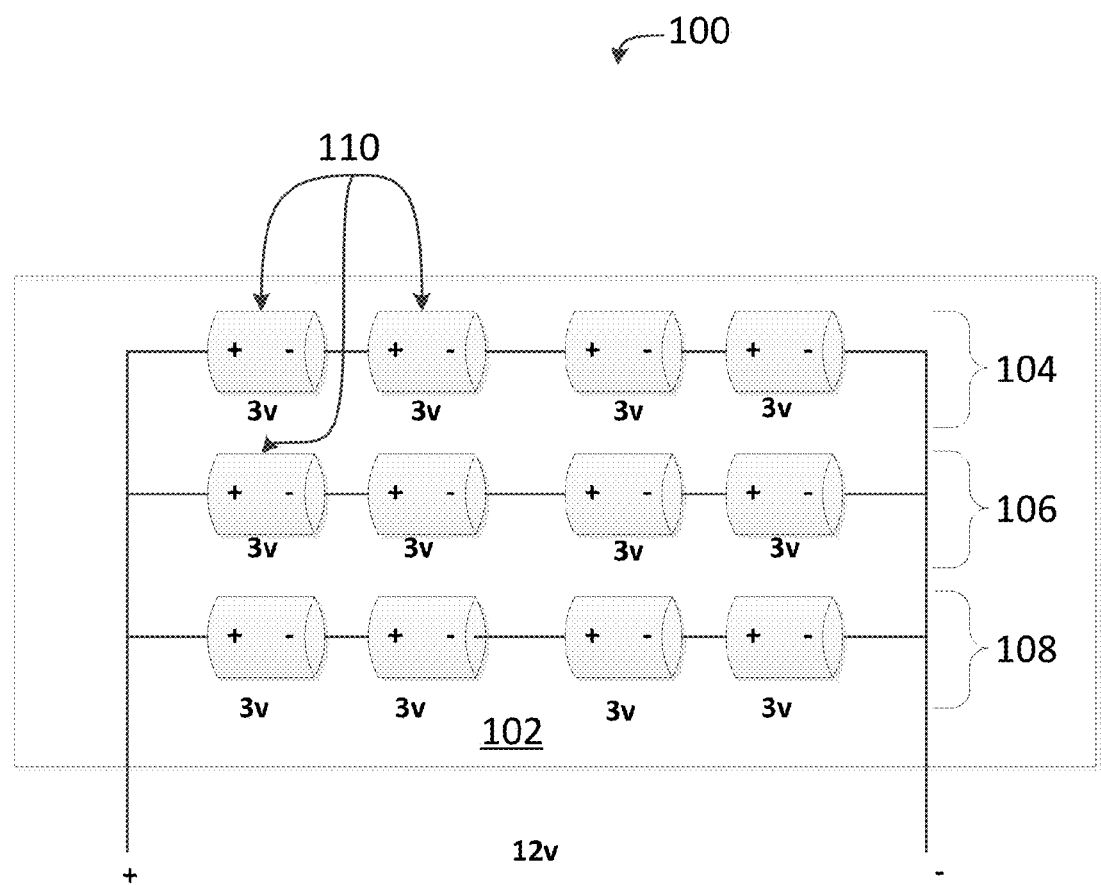
FIG. 3 shows an exemplary arrangement of battery banks and connections.

FIG. 3 shows an exemplary battery arrangement 100 for generating a 12v output using multiple 3v, Li-ion batteries 110 contained in a battery package 102. The batteries are arranged in three banks 104, 106 and 108 with each bank including four batteries 110 connected in series. Thus, the output from each of the banks is 12v (e.g., 3v/battery*4 batteries). The three banks 104, 106 and 108 are connected in parallel to generate a 12v output having a current that is about three times the current of a single bank. As such, the battery package 102 includes a single pair of connectors that provide 12v output. Assuming, for example, that each of the 3v, Li-ion batteries 110 include 0.5 g of Lithium, the total Lithium content for arrangement 100 would be 6 g (e.g., 0.5 g/battery*12 batteries). As such, based on current regulations, if one was to ship the battery arrangement 100 internationally, the shipment would be classified as a class 9 shipment and require special handling.

Figure 4B:
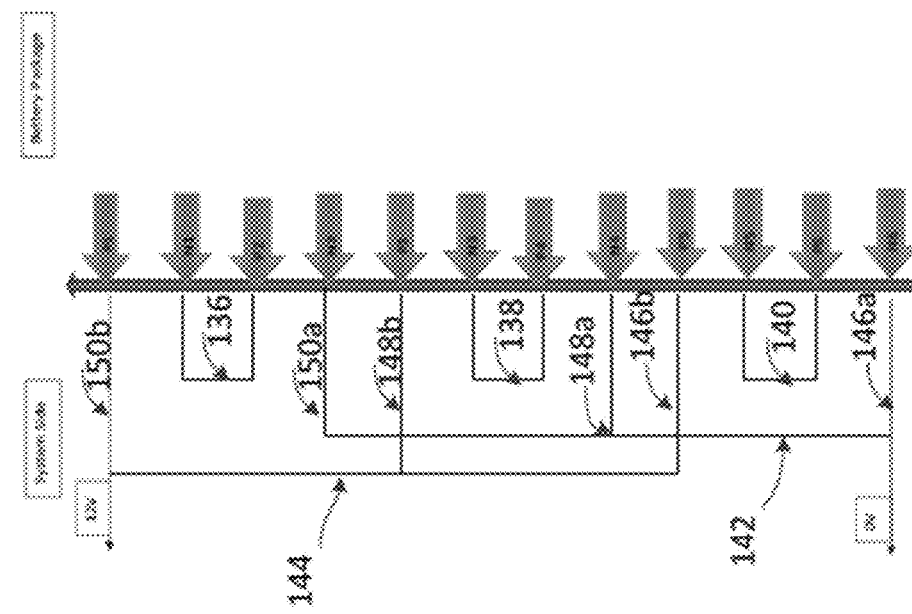
FIG. 4B shows an exemplary arrangement of electrical connections.
Figure 4A:
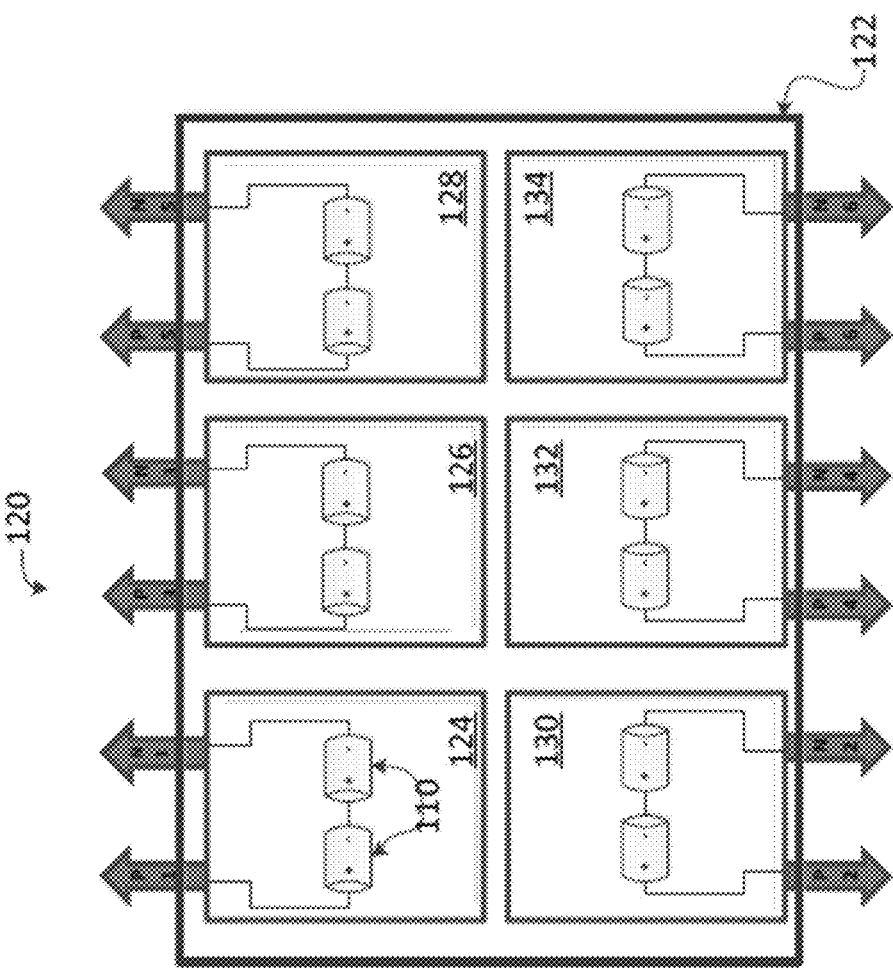
FIG. 4A shows an exemplary arrangement of battery banks and connections.

FIG. 4A shows an alternative, exemplary battery arrangement 120. Similar to the arrangement shown in FIG. 3, the battery package 122 houses twelve 3v, Li-ion batteries 110. However, in contrast to the arrangement shown in FIG. 3, the batteries are not all electrically connected to one another within the housing 122 to generate a 12v output. Rather, many of the electrical connections between the batteries 100 are omitted inside the housing 122 and are instead provided external to the battery housing 122.

The batteries in arrangement 120 are arranged in six banks 124, 126, 128, 130, 132, and 134 with each bank including two batteries 110 connected in series. Thus, the voltage output from each of the banks is 6v (e.g., 3v/battery*2 batteries). Each of the six banks 124, 126, 128, 130, 132, and 134 is associated with and electrically connected to a pair of connectors that extend from the housing 122. Thus, the banks are not electrically connected to one another within the housing 122 (e.g., each of the banks is electrically isolated from the other banks) and the battery package 122 includes a six pairs of connectors (N1,P1; N2,P2; N3,P3; N4,P4; N5,P5; N6,P6) each of which provide 6v output.

Assuming, for example, that each of the 3v, Li-ion batteries 110 includes 0.5 g of Lithium (as in the example above), the total Lithium content for arrangement 100 for shipping purposes would be 1 g (e.g., 0.5 g/battery*2 batteries) because each of the battery banks would be totaled separately due to the lack of electrical connections between the banks in the battery package 122 at the time of shipping. As such, based on current regulations, if one were to ship the battery arrangement 120, the shipment would not be classified as a class 9 shipment and would not require special handling. However, the battery package 122 also does not provide the desired 12v output. As such, connections are provided within the system packaging of the device to be powered (or within a connector device) in order to generate the 12v voltage source.

More particularly, as shown in FIG. 4B, on the system side, the system includes connectors to mate with the connectors from the battery package 122 (e.g., connectors N1, P1, N2, P2, N3, P3, N4, P4, N5, P5, N6 and P6). Inside the system packaging (e.g., inside the packaging of the device to be powered), multiple connections are formed to generate the desired 12v voltage source. For example, two banks of connectors can be connected in series (to form a series connection of four batteries) by connecting the negative terminal of one pair of connections to the positive terminal of another one of the pairs of terminals (e.g., using a wire or jumper). In the example shown in FIG. 4B, banks 124 and 130 are connected in series by wire 136, banks 126 and 132 are connected in series by wire 138 and banks 128 and 134 are connected in series by wire 140. By connecting two banks of batteries in series, the voltage of the series connection is 12v (e.g., the voltage between nodes 146a and 146b is 12v, the voltage between nodes 148a and 148b is 12v, and the voltage between nodes 150a and 150b is 12v). In order to provide a single 12v output with a greater current, the positive nodes 146b, 148b, and 150b are connected to one another (e.g., by wire 144) and the negative nodes 146a, 148a, and 150a are connected to one another (e.g., by wire 142). Thus, while the system received six different 6V inputs, connections inside the system to be powered to generate a 12v power source with the desired current.

Figure 5B:
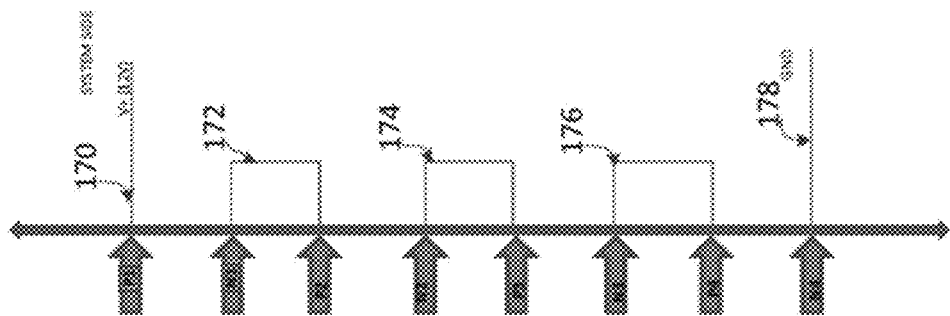
FIG. 5B shows an exemplary arrangement of electrical connections.
Figure 5A:
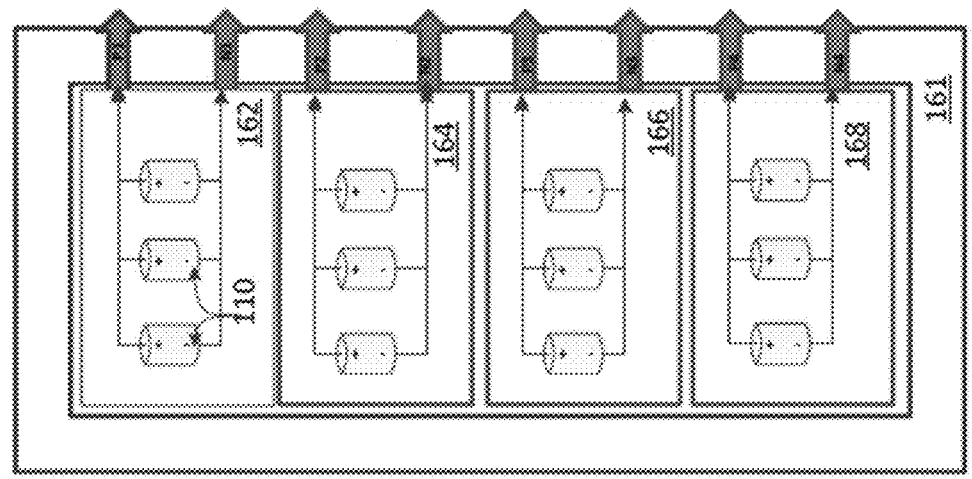
FIG. 5A shows an exemplary arrangement of battery banks and connections.

FIG. 5A shows an alternative, exemplary battery arrangement 160. Similar to the arrangement shown in FIG. 3, the battery package 122 houses twelve 3v, Li-ion batteries 110. However, in contrast to the arrangement shown in FIG. 3, the batteries are not all electrically connected to one another within the housing 122 to generate a 12v output. Rather, many of the electrical connections between the batteries 100 are omitted inside the housing 161 and are instead provided external to the battery housing 122.

The batteries in arrangement 160 are arranged in four banks 162, 164, 166, and 168 with each bank including three batteries 110 connected in parallel. Thus, for example, if the batteries each produce a 3v output, the output from each of the banks is 3v but the current is about triple the current of a single battery due to the parallel connection. Each of the four banks 162, 164, 166, and 168 is associated with a pair of connectors that extend from the housing 161. Thus, the banks are not electrically connected to one another within the housing 161 (e.g., each of the banks is electrically isolated from the other banks). As such, the battery package 161 includes a four pairs of connectors (N1,P1; N2,P2; N3,P3; N4,P4) each of which provide 3v output.

Assuming, for example, that each of the 3v, Li-ion batteries 110 includes 0.5 g of Lithium (as in the example above), the total Lithium content for arrangement 160 for shipping purposes would be 1.5 g (e.g., 0.5 g/battery*3 batteries) because each of the battery banks would be counted separately because the banks are not electrically connected in the battery package 161. As such, based on current regulations, if one were to ship the battery arrangement 160, the shipment would not be classified as a class 9 shipment and would not require special handling. However, the battery package 160 also does not provide the desired 12v output. As such, connections are provided within the system packaging of the device to be powered (or within a connector device) in order to generate the 12v voltage source.

More particularly, as shown in FIG. 5B, on the system side, the system includes connectors to mate with the connectors from the battery package 161 (e.g., to mate with connectors N1, P1, N2, P2, N3, P3, N4, and P4). Inside the system packaging (e.g., inside the packaging of the device to be powered), multiple connections are formed to generate the desired 12v voltage source. For example, the four banks can be connected in series (to form a series connection of four sets of three parallel batteries) by connecting the negative terminal of one pair of terminals to the positive terminal of another one of the pairs of terminals (e.g., using a wire or jumper). In the example shown in FIG. 5B, the negative terminal of bank 162 is connected in series by wire 172 to the positive terminal of bank 164, the negative terminal of bank 164 is connected in series by wire 174 to the positive terminal of bank 166, the negative terminal of bank 166 is connected in series by wire 176 to the positive terminal of bank 168. By connecting four banks of batteries in series, the output voltage between the positive terminal of the first bank (e.g., terminal 170) and the negative terminal of the last bank in the series connection (e.g., terminal 178) is 12v. Thus, while the system received four different 3V inputs, connections inside the system to be powered form connections to generate a 12v power source with the desired current.

While FIGS. 3, 4A-B, and 5A-B show examples of arrangements for generating a 12v source, other arrangements and voltages are possible. For example, batteries having different output voltages, lithium contents, or other characteristics can be included in the banks with the number of batteries per bank being selected such that the total lithium content is below a threshold amount of lithium. The number of banks included in the package can vary based on the connection scheme inside the connector or system and the desired voltage/current.

For example, some devices such as defibrillators operate at a certain voltage but require high current draw from batteries while other devices that operate at a certain voltage but does not require high current draw. In the case of devices that require high current draw, more banks can be added in parallel to accommodate the draw. The devices requiring lower current draw will utilize fewer banks in parallel. In some additional examples, some devices such as defibrillators require or specify a certain operating life from the battery, e.g., more Watt-hour is required. This can be accommodated by adding more battery cells.

Figure 6A:
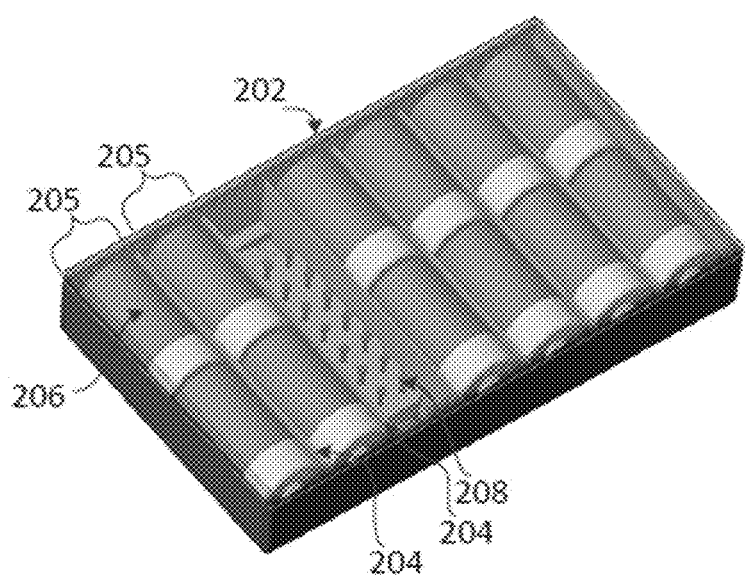
FIGS. 6A and 6B show an exemplary battery module.
Figure 6B:
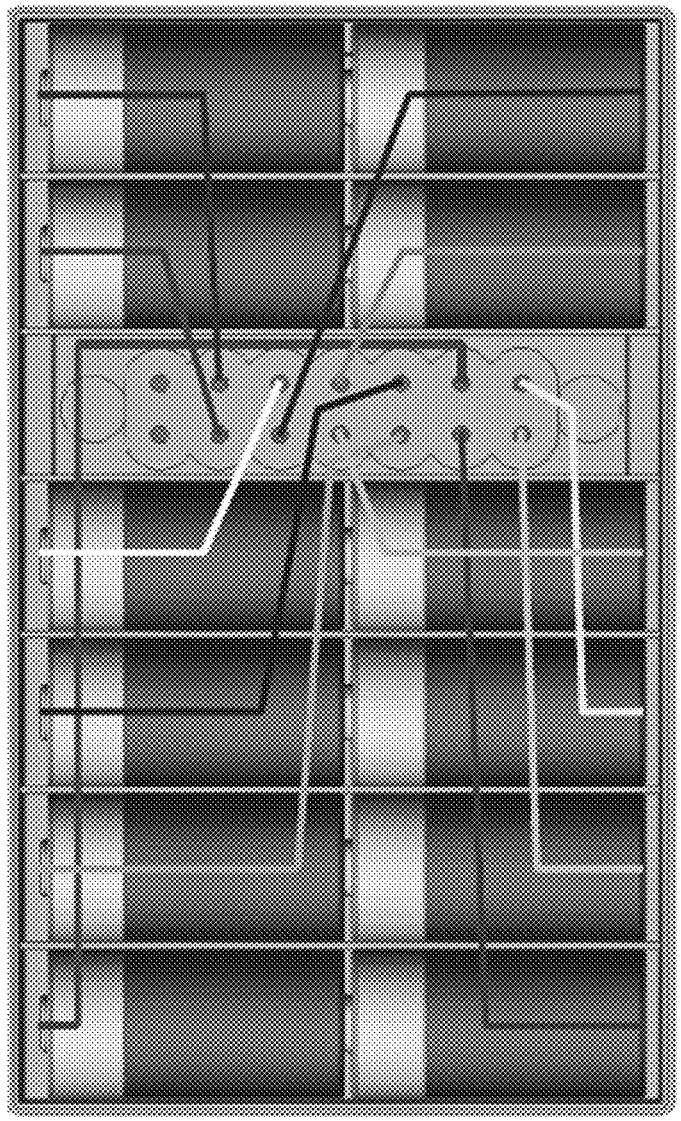

In some embodiments, banks of batteries are both electrically separated (e.g., as described above) and physically separated within a housing. FIG. 6A shows an exemplary battery package 202 housing batteries 206 arranged in banks 205 according to the arrangement shown in FIG. 4A. Each bank 205 includes spaces or cavities for the batteries 206. Electrical connections are formed between the batteries in the bank. For example the batteries in each bank in the example shown in FIG. 6A are connected in series. Each bank 205 is separated from the other banks by a divider 204. The divider can be formed of the same material as the housing 202 (e.g., plastic) and provide physical separation between the different banks. The battery package 202 also includes a connection area 208 that includes electrical connections from the banks of batteries to pins or connectors external to the housing 202. FIG. 6B shows exemplary connections (e.g., wires) between the banks 205 of batteries and the connection area 208. Thus, each of the banks is separately connected to a pair of electrical connections in the connection area 208 such that the banks are not electrically connected within the housing 202. The physical separation provided by the dividers or compartments within the housing 202 in addition to the electrical separation ensures that the lithium content of each bank of batteries is separately analyzed for compliance with shipping and transport regulations.

In some examples, the system/device to be powered is an external defibrillator for providing electrical stimulation of a patient. An external defibrillator requires a substantial current and voltage from the battery in order to provide a defibrillation shock to the patient. In order to provide the necessary voltage and current, multiple Li-ion batteries are connected to provide the voltage/current input to the device. However, the total lithium content of the batteries (if connected at the time of shipping) would be in excess of the lithium limits and require specialized shipment procedures. In order to avoid shipping restrictions, the battery unit is not connected to the defibrillator at the time of shipment and the battery unit does not have all of the connections between the lithium cells within the battery housing. Rather, the defibrillator itself is configured to connect to the battery unity using multiple connections each providing a voltage/current less than the desired total voltage/current. The defibrillator includes connection circuitry (e.g., as described herein) to form connections between banks of batteries in the battery unit. Thus, connections formed within the defibrillator itself upon connection of the battery unit to the defibrillator produce the desired voltage/current needed to power the circuitry within the defibrillator.

A number of embodiments have been described. Nevertheless, it will be understood that various modifications may be made without departing from the spirit and scope of the invention. Accordingly, other embodiments are within the scope of the following claims.

What is claimed is:

1. An external defibrillator comprising:
a unit for providing electrical stimulation to a patient;
a battery module comprising:
a housing,
a plurality of battery banks within the housing, each battery bank of the plurality of battery banks comprising two or more lithium cells, wherein a combined lithium content of the two or more lithium cells in each battery bank of the plurality of battery banks is less than 8 grams, each battery bank of the plurality of battery banks being electrically isolated from each other battery bank of the plurality of battery banks within the housing, each battery bank of the plurality of battery banks being aligned parallel to each other battery bank in the plurality of battery banks, and each battery bank of the plurality of battery banks being physically separated from each other battery bank of the plurality of battery banks by one or more corresponding dividers,
a common connection area between two adjacent battery banks of the plurality of battery banks, the common connection area comprising at least one male electrical connector including at least:
a first pair of electrical contacts electrically coupled to a first battery bank of the plurality of battery banks and electrically isolated from a second battery bank of the plurality of battery banks within the housing, and
a second pair of electrical contacts electrically coupled to the second battery bank and electrically isolated from the first battery bank within the housing,
wherein the first pair of electrical contacts and the second pair of electrical contacts terminate along an exterior of the housing and further wherein the first pair of electrical contacts and the second pair of electrical contacts are physically distinct from a battery terminal of an individual battery and are accessible from the exterior of the housing; and
a battery connection unit comprising at least one female electrical connector configured to connect to the at least one male electrical connector of the battery module to provide power to the unit for providing electrical stimulation to the patient, the battery connection unit comprising:
a third pair of electrical contacts configured to mate with the first pair of electrical contacts,
a fourth pair of electrical contacts configured to mate with the second pair of electrical contacts, and
circuitry that does not include batteries and electrically connects the third pair of electrical contacts and the fourth pair of electrical contacts and is configured to electrically connect the plurality of battery banks in the battery module in series when the battery module is connected to the battery connection unit to provide power, exclusively from the battery module, as a single voltage output to the unit for providing electrical stimulation,
wherein the third pair of electrical contacts and the fourth pair of electrical contacts terminate at the at least one female electrical connector and wherein the battery connection unit is external to the battery housing.

2. The external defibrillator of claim 1, wherein the battery connection unit is included within a housing of the unit for providing electrical stimulation.

3. The external defibrillator of claim 1, wherein the battery connection unit is separate from both a housing of the unit for providing electrical stimulation and the battery module.

4. The external defibrillator of claim 1, wherein the housing includes a plurality of physically separated compartments, each of the compartments being configured to house one battery bank of the plurality of battery banks.

5. The external defibrillator of claim 1, wherein each battery bank of the plurality of battery banks includes two or more lithium cells connected in series.

6. The external defibrillator of claim 1, wherein each battery bank of the plurality of battery banks includes two or more lithium cells connected in parallel.

7. The external defibrillator of claim 1, wherein:
the battery module includes six battery banks with each of the six battery banks including two lithium cells connected in series; and
the circuitry is configured to connect pairs of the battery banks in series and to connect the series pairs of battery banks in parallel.

8. The external defibrillator of claim 1, wherein:
the battery module includes four battery banks with each of the four battery banks including three lithium cells connected in parallel; and
the circuitry is configured to connect the four battery banks in series.

9. The external defibrillator of claim 1, wherein the total lithium content of any one of the battery banks of the plurality of battery banks is less than 2 g.

10. The external defibrillator of claim 1, wherein the total lithium content of any one of the battery banks of the plurality of battery banks is less than 3 g.

11. The external defibrillator of claim 1, wherein the circuitry electrically connecting the third and fourth pairs of electrical contacts of the battery connection unit comprises jumper wires.

12. The external defibrillator of claim 1, wherein the battery module further includes an additional pair of electrical contacts electrically coupled to a third battery bank of the plurality of battery banks and electrically isolated from the first battery bank and the second battery bank within the housing, wherein the additional pair of electrical contacts terminate along the exterior of the housing at the first common connection area.

13. The external defibrillator of claim 1, wherein the combined lithium content of the two or more lithium cells in each battery bank of the plurality of battery banks is less than 8 grams and is at least one gram.

* * * * *